(12) United States Patent
Pelletier et al.

(10) Patent No.: US 8,445,028 B2
(45) Date of Patent: May 21, 2013

(54) ECHINODERM-DERIVED EXTRACTS, METHODS OF PREPARATION AND USES THEREOF

(75) Inventors: Émilien Pelletier, Rimouski (CA); Jean Mamelona, Moncton (CA)

(73) Assignee: Rival, S.E.C., Montreal (CA)

( * ) Notice: Subject to any disclaimer, the term of this patent is extended or adjusted under 35 U.S.C. 154(b) by 287 days.

(21) Appl. No.: 12/991,267

(22) PCT Filed: May 7, 2009

(86) PCT No.: PCT/CA2009/000632
§ 371 (c)(1),
(2), (4) Date: Nov. 5, 2010

(87) PCT Pub. No.: WO2009/135311
PCT Pub. Date: Nov. 12, 2009

(65) Prior Publication Data
US 2011/0091569 A1    Apr. 21, 2011

Related U.S. Application Data

(60) Provisional application No. 61/051,824, filed on May 9, 2008.

(51) Int. Cl.
*A61K 35/12* (2006.01)
(52) U.S. Cl.
USPC .......................................................... 424/520
(58) Field of Classification Search
USPC .......................................................... 424/520
See application file for complete search history.

(56) References Cited

U.S. PATENT DOCUMENTS 6,399,105 B1    6/2002  Collin

FOREIGN PATENT DOCUMENTS

| EP | 09 74 1629 | 6/2012 |
| FR | 2679443 A1 * | 1/1993 |
| WO | WO95/37360 | 12/1995 |
| WO | WO99/37314 | 7/1999 |

OTHER PUBLICATIONS

Earle, Unit Operations in Food Processing, chap. 10, Mechanical Separations, Centrifugal Separations, New Zealand Institute of Food Science and Technology, http://www.nzifst.org.nz/unitoperations/mechseparation4.htm, 1983.*
English translation of bibliographic data and abstract of FR 2679443 A1, from PTO East database, 1993.*
Arena et al., "Evaluation of antioxidant capacity of blood orange juices as influenced by constituents, concentration process and storage", J. Food Sci. 65: 458-460 (2000).
Cao et al. "Measurement of oxygen radical absorbance capacity in biological samples", Methods in Enzymology 299: 50-62 (1999).

(Continued)

*Primary Examiner* — Rosanne Kosson
(74) *Attorney, Agent, or Firm* — Goudreau Gage Dubuc; S. Serge Shahinian; Alain Dumont

(57) ABSTRACT

An Echinozoa tissue or organ extract comprising antioxidant compounds is disclosed. Also disclosed is a process for obtaining an Echinozoa tissue or organ extract, as well an extract obtained by this process. Compositions comprising such an extract are also described. Uses of such extracts/compositions, as well as corresponding methods of treatment, for example as an antioxidant or to decrease or inhibit oxidative stress in a cell, tissue or subject are also described.

21 Claims, 1 Drawing Sheet

OTHER PUBLICATIONS

Castell et al., "Effect of dietary lipids on fatty acid composition and metabolism in juvenile green sea urchins", Aquaculture, 242:417-435 (2004).

Dionex Corporation, "Accelerated solvent extraction techniques for in-line selective removal of interferences" (2007).

Herrero et al., "Pressurized liquid extracts from Spiruline platensis microalga determination of their antioxidant activity and preliminary analysis by micellar electrokinetic chromatography", J. Chromatogr. A. 1047(2): 195-203 (2004).

Herrero et al., "Optimization of the extraction of antioxidants from *Dunaliella salina* Microalga by pressurized liquids", J. Agric. Food Chem. 54(15): 5597-5603 (2006).

Kohen et al., "Invited review: oxidation of biological systems: oxidative stress phenomena, antioxidants, redox reactions, and method for their quantification", Toxicologic Pathology 30: 620-650 (2002).

Lee et al., "Reactive oxygen species, aging, and antioxidative nutraceuticals", Comprehensive Reviews of Food Science and Food Safety 3: 21-33 (2004).

Lovaas et al., "High troughput screening for antioxidants in marine organisms", unknown publication date, as early as Apr. 2006.

Mamelona et al., "Quantification of phenolic contents and antioxidant capacity of Atlantic sea cucumber", Food Chemistry, 104:1040-1047 (2007).

Ou et al., "Development and validation of an improved oxygen radical absorbance capacity assay using fluorescein as the fluorescent probe", J. Agric. Food Chem. 49: 4619-4626 (2001).

Pandjaitan, N, "Pressurized liquid extraction of phenolics from spinach", 2002 Annual Meeting and Food Expo, Anaheim, California (2002).

Santoyo et al., "Functional characterization of pressurized liquid extracts of spirulina platensis", Eur. Food Res. and Technol. A. 224(1):75-81 (2006).

Sheean et al., "Bioactivity of extracts from gonadal tissue of the edible Australian purple urchin", J. Sci. Food Agric., 87:694-701 (2007).

Singleton et al., "Analysis of total phenols and other oxidation substrates and antioxidants by means of folin-ciocalteu reagent", Methods in Enzymology 299: 152-178 (1999).

Symonds et al., "Carotenoids in the sea urchin *Paracentrotus lividus*: occurrence of 9'-cis-echinenone as the dominant carotenoid in gonad colour determination", Comp. Biochem. Physiol. B 148: 432-444 (2007).

Wu et al., "Lipophilic and Hydrophilic Antioxidant Capacities of Common Foods in the United States", J. Agric. Food Chem., 52:4026-4037 (2004).

Zhong et al., "Compositional characteristics and antioxidant properties of fresh and processed sea cucumber", J. Agric. Food Chem., 55:1188-1192 (2007).

Fredalina et al., "Fatty acid compositions in local sea cucumber, *Stichopus chloronotus*, for wound healing", General Pharmacoly, 33:4: 337-340 (1999).

* cited by examiner

A
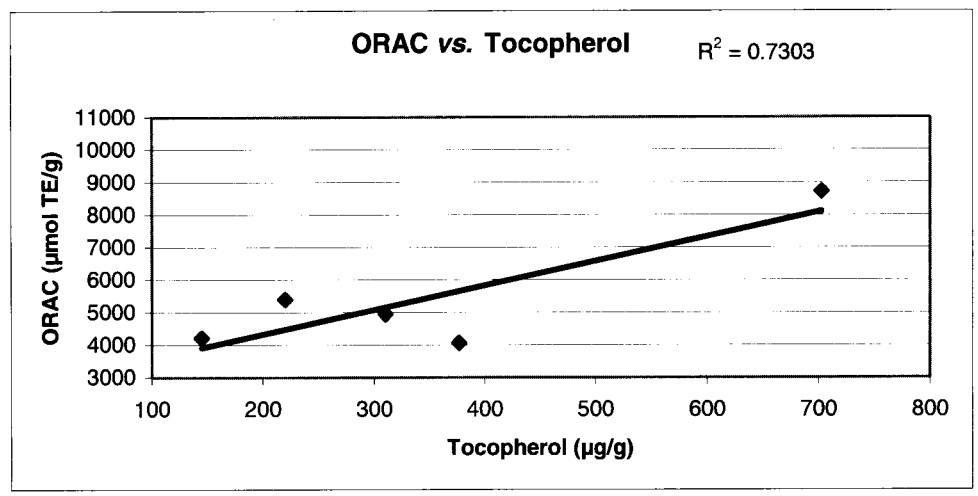
B
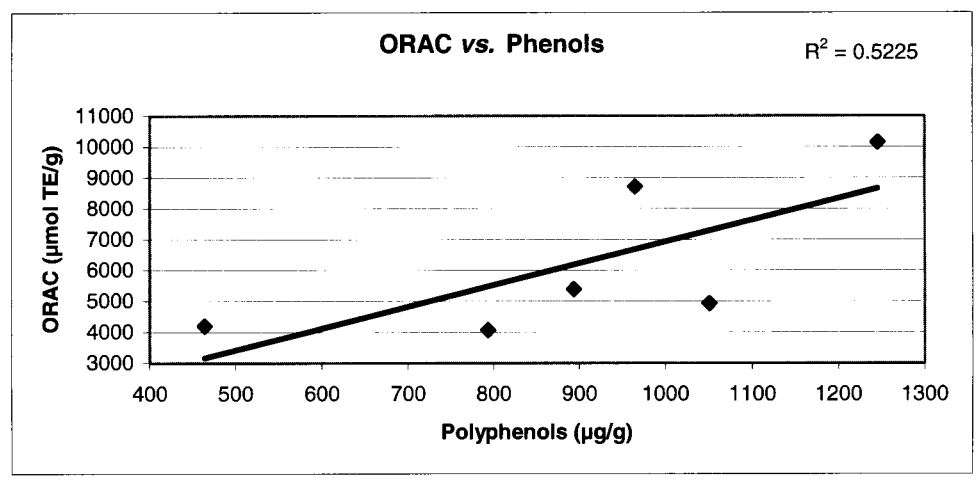
C
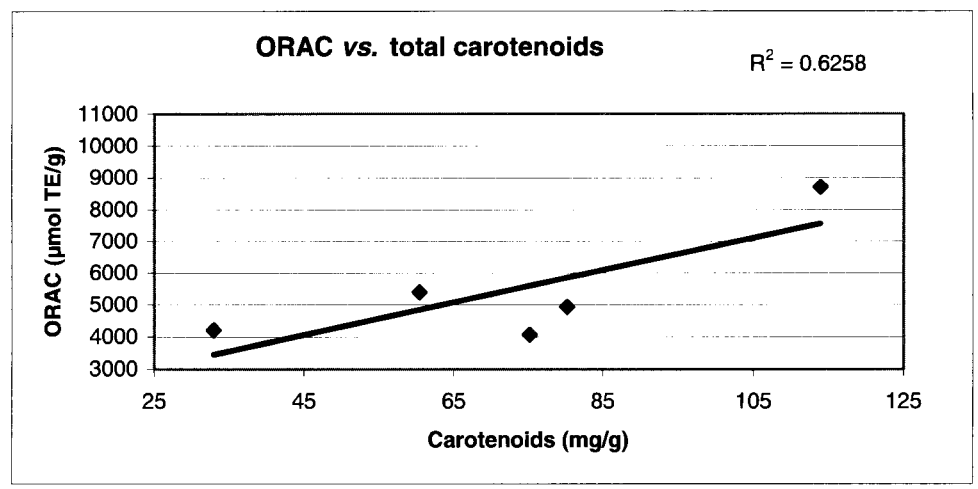

ECHINODERM-DERIVED EXTRACTS, METHODS OF PREPARATION AND USES THEREOF

CROSS REFERENCE TO RELATED APPLICATIONS

This application is a U.S. National Phase Application of PCT application no PCT/CA2009/000632, filed on May 7, 2009, and published in English under PCT Article 21(2), which itself claims the benefit, under 35 U.S.C. §119(e), of U.S. provisional application Ser. No. 61/051,824 filed on May 9, 2008. All documents above are incorporated herein by reference in their entirety.

TECHNICAL FIELD

The present invention generally relates to extracts obtained from marine invertebrates. More specifically, the present invention relates to extracts obtained from echinoderm tissues/organisms.

BACKGROUND ART

Reactive oxygen species (ROS) are toxic radicals generated by the process of oxidation during normal cell metabolism. Elevated or uncontrolled production of ROS is associated with a variety of diseases or disorders such as cataracts, heart disease, cancer, inflammatory diseases, male infertility, aging, and various neurodegenerative diseases such as Alzheimer's disease, amyotrophic lateral sclerosis, Parkinson's disease, multiple sclerosis and aging. ROS often leads to damage of cellular macromolecules (nucleic acid, proteins and lipids), and thus inflict direct tissue damage. Antioxidants, such as those found in food and supplements, support human intrinsic antioxidative protection to maintain the internal oxidation status by various processes such as in situ regeneration of antioxidant molecules (vitamins and enzymes) or direct neutralization of oxidative compounds (Kohen & Nyska, 2002. *Toxicologic Pathology* 30: 620-650; Lee et al., 2004. *Comprehensive Reviews of Food Science and Food Safety* 3: 21-33).

There is thus a need for novel products having antioxidant properties.

The present description refers to a number of documents, the content of which is herein incorporated by reference in their entirety.

SUMMARY OF THE INVENTION

The present invention relates to extracts obtained from echinoderm tissues/organisms. Echinoderms are a phylum of invertebrate marine animals found at all ocean depths. Echinoderms are divided into five different classes, namely Asteroidea, Ophiuroidea, Echinoidea (Sea Urchins), Crinoidea and Holothuroidea (Sea Cucumbers). Echinoidea and Holothuroidea form a subphylum known as Echinozoa. The sea cucumber *Cucumaria frondosa* (Atlantic Sea Cucumber) is found in North Atlantic shallow waters and is harvested mainly for food purposes in Maine and Canada. The sea urchin *Strongylocentrotus droebachiensis* (Green Sea Urchin) is found widespread on the northern hemisphere, and has also been harvested by man as a food source for thousands of years.

In a first aspect, the present invention provides an Echinozoa tissue or organ extract having:

(a) an Oxygen Radical Absorption Capacity (ORAC) value higher than 2700 micromolar of Trolox™ equivalent per gram of the dry extract (μmol TE/g dry extract);
(b) an eicosapentaenoic acid (EPA) to docosahexaenoic acid (DHA) ratio of at least about 4 [weight/weight (w/w)];
(c) an eicosapentaenoic acid (EPA) content of at least about 10% of the total fatty acid content of the extract (w/w);
(d) an omega-3 (ω-3) to omega-6 (ω-6) fatty acid ratio of at least about 1.6 (w/w); or
(e) any combination of (a) to (d).

In another aspect, the present invention provides an Echinozoa tissue or organ extract having an Oxygen Radical Absorption Capacity (ORAC) value higher than 2700 micromolar of Trolox™ equivalent per gram of the dry extract (μmol TE/g dry extract). In an embodiment, the above-mentioned extract has an eicosapentaenoic acid (EPA) to docosahexaenoic acid (DHA) ratio of at least about 4 (w/w). In an embodiment, the above-mentioned extract has an eicosapentaenoic acid (EPA) content of at least about 10% of the total fatty acid content of the extract (w/w). In an embodiment, the above-mentioned extract has an omega-3 (ω-3) to omega-6 (ω-6) fatty acid ratio of at least about 1.6 (w/w).

In another aspect, the present invention provides an Echinozoa tissue or organ extract having an eicosapentaenoic acid (EPA) to docosahexaenoic acid (DHA) ratio of at least about 4 (w/w). In an embodiment, the above-mentioned extract has an eicosapentaenoic acid (EPA) content of at least about 10% of the total fatty acid content of the extract (w/w). In another embodiment, the above-mentioned extract has an ORAC value higher than 2700 μmol TE/g dry extract. In an embodiment, the above-mentioned extract has an omega-3 (ω-3) to omega-6 (ω-6) fatty acid ratio of at least about 1.6 (w/w).

In another aspect, the present invention provides an Echinozoa tissue or organ extract having an eicosapentaenoic acid (EPA) content of at least about 10% of the total fatty acid content (w/w). In an embodiment, the above-mentioned extract has an eicosapentaenoic acid (EPA) to docosahexaenoic acid (DHA) ratio of at least about 4 (w/w). In another embodiment, the above-mentioned extract has an ORAC value higher than 2700 μmol TE/g dry extract. In an embodiment, the above-mentioned extract has an omega-3 (ω-3) to omega-6 (ω-6) fatty acid ratio of at least about 1.6 (w/w).

In another aspect, the present invention provides an Echinozoa tissue or organ extract having an omega-3 (ω-3) to omega-6 (ω-6) fatty acid ratio of at least about 1.6 (w/w). In an embodiment, the above-mentioned extract has an eicosapentaenoic acid (EPA) content of at least about 10% of the total fatty acid content (w/w). In an embodiment, the above-mentioned extract has an eicosapentaenoic acid (EPA) to docosahexaenoic acid (DHA) ratio of at least about 4 (w/w). In another embodiment, the above-mentioned extract has an ORAC value higher than 2700 μmol TE/g dry extract.

In another aspect, the present invention provides an Echinozoa tissue or organ extract obtained by pressurized liquid extraction (PLE) using a $C_1$-$C_3$ alcohol as a solvent.

In another aspect, the present invention provides an Echinozoa tissue or organ extract obtained by a process comprising:

(a) providing (e.g., ground) Echinozoa tissue or organ;
(b) mixing said (e.g., ground) tissue or organ with a dispersing agent; and
(c) submitting said mixture to pressure liquid extraction (PLE) in the presence of an alcohol.

In another aspect, the present invention provides a process for preparing an Echinozoa tissue or organ extract comprising:
(a) providing (e.g., ground) Echinozoa tissue or organ;
(b) mixing said (e.g., ground) tissue or organ with a dispersing agent; and
(c) submitting said mixture to pressure liquid extraction (PLE) in the presence of an alcohol.

In an embodiment, the above-mentioned PLE is high-pressure liquid extraction (HPLE).

In another embodiment, the above-mentioned process further comprises (d) evaporating the solvent from the extract of step (c).

In an embodiment, the above-mentioned process further comprises freeze-drying or dehydrating said Echinozoa tissue or organ before step (a).

In an embodiment, the above-mentioned dispersing agent is a silica-based dispersing agent. In a further embodiment, the above-mentioned dispersing agent is diatomaceous earth.

In an embodiment, the tissue or organ/dispersing agent ratio is from about 1/10 to about 1/30 (w/w). In a further embodiment, the above-mentioned tissue or organ/dispersing agent ratio is about 1/22 (w/w).

In another embodiment, the above-mentioned extraction is performed at a temperature of about 40° C. to about 80° C. In a further embodiment, the above-mentioned extraction is performed at a temperature of about 40° C. to about 60° C. In a further embodiment, the above-mentioned extraction is performed at about 60° C.

In an embodiment, the above-mentioned alcohol is an alcohol of formula I:

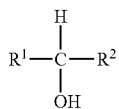

(I)

wherein $R^1$ and $R^2$ are each independently $CH_3$ or H;
or any combination of (i) an alcohol of formula I wherein $R^1$ and $R^2$ are H, (ii) an alcohol of formula I wherein $R^1$ is $CH_3$ and $R^2$ is H, and (iii) an alcohol of formula I wherein $R^1$ and $R^2$ are $CH_3$.

In an embodiment, $R^1$ and $R^2$ are H.
In another embodiment, $R^1$ is $CH_3$ and $R^2$ is H.
In another embodiment, $R^1$ and $R^2$ are $CH_3$.

In an embodiment, the above-mentioned alcohol is (i) methanol, (ii) ethanol, (iii) isopropanol or (iv) any combination of (i) to (iii). In a further embodiment, the above-mentioned alcohol is ethanol, isopropanol, or a combination thereof.

In an embodiment, the above-mentioned extract has an ORAC value higher than 800 µmol TE/g dry extract. In a further embodiment, the above-mentioned extract has an ORAC value higher than 2700 µmol TE/g dry extract.

In an embodiment, the above-mentioned extract has an eicosapentaenoic acid (EPA) to docosahexaenoic acid (DHA) ratio of at least about 4 (w/w).

In an embodiment, the above-mentioned extract has an eicosapentaenoic acid (EPA) content of at least about 10% of the total fatty acid content of the extract (w/w).

In an embodiment, the above-mentioned extract has an omega-3 (ω-3) to omega-6 (ω-6) fatty acid ratio of at least about 1.6 (w/w).

In another embodiment, the above-mentioned tissue or organ is (i) a gonad, (ii) a tissue or organ of the digestive tract, (iii) a viscera, or (iv) any combination of (i) to (iii).

In an embodiment, the above-mentioned Echinozoa is of the Holothuroidea or Echinoidea class.

In another embodiment, the above-mentioned Holothuroidea is of the *Cucumaria* genus. In a further embodiment, the above-mentioned Holothuroidea of the *Cucumaria* genus is *Cucumaria frondosa*.

In another embodiment, the above-mentioned Echinoidea is of the *Strongylocentrotus* genus. In a further embodiment, the above-mentioned Echinozoa of the *Strongylocentrotus* genus is *Strongylocentrotus droebachiensis*.

In an embodiment, the above-mentioned extract comprises (i) at least 100 µg of α-Tocopherol per gram of extract, (ii) at least 10 mg of carotenoids per gram of extract, (iii) at least 400 µg of phenols per gram of extract, or (iv) any combination of (i) to (iii).

In another aspect, the present invention provides a composition comprising the above-mentioned extract and a carrier. In an embodiment, the above-mentioned composition is an antioxidant composition.

In another aspect, the present invention provides a use of (i) the above-mentioned extract, (ii) the above-mentioned composition, or (iii) a combination of (i) and (ii), as a medicament.

In another aspect, the present invention provides a use of (i) the above-mentioned extract, (ii) the above-mentioned composition, or (iii) a combination of (i) and (ii), for the preparation of a medicament.

In another aspect, the present invention provides a use of (i) the above-mentioned extract, (ii) the above-mentioned composition, or (iii) a combination of (i) and (ii) as an antioxidant.

In another aspect, the present invention provides a use of (i) the above-mentioned extract, (ii) the above-mentioned composition, or (iii) a combination of (i) and (ii), for decreasing or inhibiting oxidative stress in a cell or tissue.

In another aspect, the present invention provides a use of (i) the above-mentioned extract, (ii) the above-mentioned composition, or (iii) a combination of (i) and (ii), for prevention or treatment of a condition associated with oxidative stress.

In another aspect, the present invention provides a use of (i) the above-mentioned extract, (ii) the above-mentioned composition, or (iii) a combination of (i) and (ii), for the preparation of an antioxidant medicament.

In another aspect, the present invention provides a use of (i) the above-mentioned extract, (ii) the above-mentioned composition, or (iii) a combination of (i) and (ii), for the preparation of a medicament for decreasing or inhibiting oxidative stress in a cell or tissue.

In another aspect, the present invention provides a use of (i) the above-mentioned extract, (ii) the above-mentioned composition, or (iii) a combination of (i) and (ii), for the preparation of a medicament for prevention or treatment of a condition associated with oxidative stress.

In another aspect, the present invention provides (i) the above-mentioned extract, (ii) the above-mentioned composition, or (iii) a combination of (i) and (ii), for use as an antioxidant.

In another aspect, the present invention provides (i) the above-mentioned extract, (ii) the above-mentioned composition, or (iii) a combination of (i) and (ii), for use in decreasing or inhibiting oxidative stress in a cell or tissue.

In another aspect, the present invention provides (i) the above-mentioned extract, (ii) the above-mentioned composition, or (iii) a combination of (i) and (ii), for use in prevention or treatment of a condition associated with oxidative stress.

In another aspect, the present invention provides a method of decreasing or inhibiting oxidative stress in a cell or tissue comprising contacting said cell or tissue with (i) the above-mentioned extract, (ii) the above-mentioned composition, or (iii) a combination of (i) and (ii).

In another aspect, the present invention provides a method for preventing or treating a condition associated with oxidative stress in a subject, said method comprising administering to said subject (i) the above-mentioned extract, (ii) the above-mentioned composition, or (iii) a combination of (i) and (ii).

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:

FIG. 1 shows the correlation between Oxygen Radical Absorption Capacity (ORAC) values and content of various antioxidant compounds in the extracts;

DISCLOSURE OF INVENTION

In the studies described herein, it is shown that extracts having antioxidant properties may be obtained from various organs and tissues of marine invertebrates belonging to the Echinozoa subphylum.

Accordingly, in a first aspect, the present invention provides a process for preparing an Echinozoa tissue or organ extract comprising:
(a) providing (e.g., ground) Echinozoa tissue or organ;
(b) mixing said tissue or organ with a dispersing agent; and
(c) submitting said mixture to pressure liquid extraction (PLE) in the presence of an alcohol.

The starting material (i.e. Echinozoa tissue or organ) may be ground/crushed or otherwise broken or sheared into smaller pieces using any method (or device) known in the art, for example using a commercially-available grinders or comparable devices. In an embodiment, the above-mentioned Echinozoa tissue or organ is dehydrated before step (a). The term "dehydrated" or "dehydration" as used herein is intended to mean passive or active dehydration of the Echinozoa tissue or organ as defined above. Simple air-drying, dessication, vacuum assisted dehydration (e.g., freeze-drying), warming, water sublimation or other methods may perform the dehydration. In an embodiment, the starting material is dehydrated by freeze-drying before being ground/crushed or otherwise broken up. The ground/crushed material may be stored, preferably in the dark, before extraction. In an embodiment, the ground/crushed material is kept frozen (e.g., at about −20° C.) before extraction.

The ground/crushed organ or tissue may be mixed with a dispersing agent. The main function of the dispersing agent is to facilitate the distribution of the biological material along the extraction cell and to increase the contact surface with the solvent. Therefore, any agent that can perform this function without interfering with the extraction process (e.g., chemically inert) may be used in the process of the present invention. In an embodiment, the dispersing agent is a silica-based dispersing agent (e.g., Ottawa silica sand, Celite™ 545). In an embodiment, the above-mentioned dispersing agent is diatomaceous earth. In another embodiment, the tissue or organ/dispersing agent ratio is from about 1/10 to about 1/30 (w/w). In another embodiment, the tissue or organ/dispersing agent ratio is from about 1/15 to about 1/25 (w/w). In a further embodiment, the tissue or organ/dispersing agent ratio is about 1/22 (w/w).

The extraction process is performed in the presence of a solvent, such as an alcohol or polyol (or any combination/mixture thereof). The alcohol or polyol solvent may be mixed with water for the extraction (e.g., to obtain an hydroalcoholic or hydropolyolic mixture).

In an embodiment, the above-mentioned alcohol is a $C_1$-$C_3$ alcohol. In a further embodiment, the above-mentioned $C_1$-$C_3$ alcohol is of formula I:

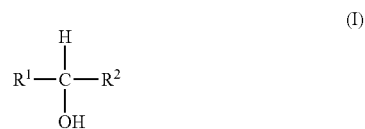

wherein $R^1$ and $R^2$ are each independently $CH_3$ or H;
or any combination of (i) an alcohol of formula I wherein $R^1$ and $R^2$ are H, (ii) an alcohol of formula I wherein $R^1$ is $CH_3$ and $R^2$ is H, and (iii) an alcohol of formula I wherein $R^1$ and $R^2$ are $CH_3$.

In an embodiment, $R^1$ and $R^2$ are H.
In another embodiment, $R^1$ is $CH_3$ and $R^2$ is H.
In another embodiment, $R^1$ and $R^2$ are $CH_3$.

In an embodiment, the above-mentioned alcohol or polyol is (i) methanol, (ii) ethanol, (iii) isopropanol, (iv) any combination of (i) to (iii). In a further embodiment, the above-mentioned alcohol or polyol is ethanol, isopropanol, or a combination thereof.

The extraction process (e.g., pressure liquid extraction, PLE) may be carried out using any suitable extractor (e.g., commercially available extractors), such as the Dionex™ ASE-200 extractor (Dionex Corporation, Sunnyvale, Calif., USA). In an embodiment, the above-mentioned extraction is performed by high-pressure liquid-solid extraction (HPLE). As used herein, HPLE refers to an extraction performed under a pressure of at least about 100 psi in short times and with low amounts of solvent. In an embodiment, the extraction is performed in less than about 7.5 ml of solvent per 100 mg of sample (extract). In an embodiment, the above-mentioned pressure is less than about 2500 psi. In a further embodiment, the above-mentioned pressure is about 1500 psi. In another embodiment, the above-mentioned HPLE is performed based on the method of Richter et al. (U.S. Pat. No. 5,843,311). In another embodiment, the above-mentioned HPLE is performed using the conditions/parameters set forth in Table I below. In another embodiment, the above-mentioned extraction is performed at a temperature of about 40° C. to about 80° C. In another embodiment, the above-mentioned extraction is performed at a temperature of about 40° C. to about 60° C. In a further embodiment, the above-mentioned extraction is performed at a temperature of about 60° C.

The extract obtained is typically in the form of a liquid concentrate. The concentrate may then be dried (e.g., evaporation of the extraction solvent) using apparatus and methods well known in the art, to obtain a solid or dry extract. In an embodiment, the liquid extract is dried via gaseous flow, e.g., under the flow of an inert gas, e.g., under (e.g., continuous) nitrogen flow. In another embodiment, the liquid extract is dried via evaporation, e.g., using a rotating evaporator or similar device. In another embodiment, the liquid extract is dried at ambient temperature (e.g., between about 15° C. to about 30° C., and more particularly between about 20° C. to about 25° C.).

The extraction process may be repeated one or more times. In an embodiment, one or more of the extraction step(s) is/are performed under low light intensity.

In another aspect, the present invention provides an Echinozoa tissue or organ extract obtained by the above-mentioned process.

In another aspect, the present invention provides an Echinozoa tissue or organ extract obtained by pressurized liquid extraction (PLE) using alcohol as a solvent.

In an embodiment, the above-mentioned extract has an Oxygen Radical Absorption Capacity (ORAC) value higher than 800 micromolar of Trolox™ equivalent per gram of the dry extract (μmol TE/g dry extract).

In another aspect, the present invention provides an Echinozoa tissue or organ extract having:
 (a) an Oxygen Radical Absorption Capacity (ORAC) value higher than 2700 micromolar of Trolox™ equivalent per gram of the dry extract (μmol TE/g dry extract);
 (b) an eicosapentaenoic acid (EPA) to docosahexaenoic acid (DHA) ratio of at least about 4 (w/w);
 (c) an eicosapentaenoic acid (EPA) content of at least about 10% of the total fatty acid content (w/w);
 (d) an omega-3 (ω-3) to omega-6 (ω-6) fatty acid ratio of at least about 1.6 (w/w); or
 (e) any combination of (a) to (d).

In another aspect, the present invention provides an Echinozoa tissue or organ extract having an Oxygen Radical Absorption Capacity (ORAC) value higher than 2700 micromolar of Trolox™ equivalent per gram of the dry extract (μmol TE/g dry extract). In an embodiment, the above-mentioned extract has an eicosapentaenoic acid (EPA) to docosahexaenoic acid (DHA) ratio of at least about 4 (w/w). In an embodiment, the above-mentioned extract has an eicosapentaenoic acid (EPA) content of at least about 10% of the total fatty acid content of the extract (w/w). In an embodiment, the above-mentioned extract has an omega-3 (ω-3) to omega-6 (ω-6) fatty acid ratio of at least about 1.6 (w/w).

In another aspect, the present invention provides an Echinozoa tissue or organ extract having an eicosapentaenoic acid (EPA) to docosahexaenoic acid (DHA) ratio of at least about 4 (w/w). In an embodiment, the above-mentioned extract has an eicosapentaenoic acid (EPA) content of at least about 10% of the total fatty acid content of the extract (w/w). In another embodiment, the above-mentioned extract has an ORAC value higher than 2700 μmol TE/g dry extract. In an embodiment, the above-mentioned extract has an omega-3 (ω-3) to omega-6 (ω-6) fatty acid ratio of at least about 1.6 (w/w).

In another aspect, the present invention provides an Echinozoa tissue or organ extract having an eicosapentaenoic acid (EPA) content of at least about 10% of the total fatty acid content (w/w). In an embodiment, the above-mentioned extract has an eicosapentaenoic acid (EPA) to docosahexaenoic acid (DHA) ratio of at least about 4 (w/w). In another embodiment, the above-mentioned extract has an ORAC value higher than 2700 μmol TE/g dry extract. In an embodiment, the above-mentioned extract has an omega-3 (ω-3) to omega-6 (ω-6) fatty acid ratio of at least about 1.6 (w/w).

In another aspect, the present invention provides an Echinozoa tissue or organ extract having an omega-3 (ω-3) to omega-6 (ω-6) fatty acid ratio of at least about 1.6 (w/w). In an embodiment, the above-mentioned extract has an eicosapentaenoic acid (EPA) content of at least about 10% of the total fatty acid content (w/w). In an embodiment, the above-mentioned extract has an eicosapentaenoic acid (EPA) to docosahexaenoic acid (DHA) ratio of at least about 4 (w/w). In another embodiment, the above-mentioned extract has an ORAC value higher than 2700 μmol TE/g dry extract.

The Oxygen Radical Absorption Capacity (ORAC) assay is commonly used to measure the antioxidative capacity of various antioxidants. The ORAC assay provides an effective measure of antioxidant protection afforded to physiologically important biomolecules such as proteins. ORAC assays that may be used in the present invention include, for example, those described in U.S. Pat. No. 6,060,324, Methods in Enzymology (1999) 299: 50-62 (Cao and Prior), and Ou et al., 2001. J. Agric. Food Chem. 49: 4619-4626. In an embodiment, the ORAC values are determined using the ORAC assay described in Example 2 below.

In the assays of the examples described below, the ORAC response is normalized to a chemical called Trolox™, also known as 6-hydroxy-2,5,7,8-tetramethylchroman-2-carboxylic acid, a water soluble Vitamin E analog often used in free radical assays. Unless otherwise stated, the ORAC values are expressed as a Trolox™ equivalent value per gram of extract.

In an embodiment, the above-mentioned ORAC value is at least about 2700. In a further embodiment, the above-mentioned ORAC value is at least about 3000. In a further embodiment, the above-mentioned ORAC value is at least about 4000. In a further embodiment, the above-mentioned ORAC value is at least about 5000. In a further embodiment, the above-mentioned ORAC value is at least about 6000. In a further embodiment, the above-mentioned ORAC value is at least about 7000. In a further embodiment, the above-mentioned ORAC value is at least about 8000.

In another embodiment, the above-mentioned EPA to DHA ratio is at least about 5 (w/w), in further embodiments at least about 6, 7, 8, 9, 10, 15, 20, 30, 40, 50, 60, 70, 80, 90, 100, 110, 120, 130 or 140 (w/w).

In another embodiment, the above-mentioned EPA content is at least about 12% of the total fatty acid content (w/w), in further embodiments at least about 14%, 16%, 18%, 20%, 22%, 24%, 26% or 28% (w/w).

In another embodiment, the above-mentioned ω-3 to ω-6 fatty acid ratio is at least about 1.8 (w/w), in further embodiments at least about 2, 2.2, 2.4, 2.6, 2.8, 3, 3.5, 4, 4.5, 5, 5.5 or 6 (w/w).

Methods to measure the levels of fatty acids, such as alpha-linolenic acid (ALA), eicosapentaenoic acid (EPA) and docosahexaenoic acid (DHA), in a sample (e.g., an extract) are well known in the art, and may be performed for example as described in the Examples below.

Any tissue or organ, or any combinations thereof, obtained from any genus/species belonging to the Echinozoa subphylum may be used as starting material in the process of the present invention (e.g., gonads, digestive tract, viscera, muscles, respiratory tract). For example, the starting material may be collected from the processing wastes of the food industry (e.g., sea urchin or sea cucumber industry). In an embodiment, the above-mentioned tissue or organ is (i) a gonad, (ii) a tissue or organ of the digestive tract, (iii) a viscera, or (iv) any combination of (i) to (iii).

In an embodiment, the above-mentioned Echinozoa is of the Holothuroidea or Echinoidea class. In a further embodiment, the above-mentioned Holothuroidea is of the *Cucumaria* genus. In a further embodiment, the above-mentioned Holothuroidea of the *Cucumaria* genus is *Cucumaria frondosa* (Atlantic sea cucumber). In another embodiment, the above-mentioned Echinoidea is of the *Strongylocentrotus* genus. In a further embodiment, the above-mentioned Echinozoa of the *Strongylocentrotus* genus is *Strongylocentrotus droebachiensis* (green sea urchin).

The extract of the present invention is enriched in compounds having antioxidant properties. In an embodiment, the above-mentioned extract comprises (i) at least 100 µg of α-Tocopherol per gram of extract, (ii) at least 10 mg of carotenoids per gram of extract, (iii) at least 400 µg of phenols per gram of extract, or (iv) any combination of (i) to (iii).

In another aspect, the present invention provides a composition or formulation (e.g., an antioxidant composition or formulation) comprising the above-mentioned extract and a carrier or excipient (e.g., a pharmaceutically acceptable, cosmetically acceptable, or a consumable carrier/excipient).

In various embodiments, an extract of the invention may be used therapeutically in formulations or medicaments to prevent or treat a condition, such as a condition associated with oxidative stress. The invention provides corresponding methods of medical treatment, in which a therapeutic dose of an extract of the invention is administered in a pharmacologically acceptable formulation, e.g. to a patient or subject in need thereof. Accordingly, the invention also provides therapeutic compositions comprising an extract of the invention and a pharmacologically acceptable excipient or carrier.

A "therapeutically effective amount" or "effective amount" (in the context of treatment) refers to an amount effective, at dosages and for periods of time necessary, to achieve the desired therapeutic result, such as a reduction of oxidative stress and in turn a reduction in progression of or the amelioration of an associated condition. A therapeutically effective amount may vary according to factors such as the disease state, age, sex, and weight of the individual, and the ability of the compound to elicit a desired response in the individual. Dosage regimens may be adjusted to provide the optimum therapeutic response. A therapeutically effective amount is also one in which any toxic or detrimental effects of the compound are outweighed by the therapeutically beneficial effects. A "prophylactically effective amount" or "effective amount" (in the context of prevention) refers to an amount effective, at dosages and for periods of time necessary, to achieve the desired prophylactic result, such as preventing or inhibiting the rate of disease onset or progression of a condition associated with oxidative stress. A prophylactically effective amount can be determined as described above for the therapeutically effective amount. For any particular subject, specific dosage regimens may be adjusted over time according to the individual need and the professional judgement of the person administering or supervising the administration of the compositions.

The extract or composition of the present invention may be administered in any number of conventional dosage forms, e.g., topical, oral, parenteral, rectal, transdermal, and the like. Oral or rectal dosage forms include capsules, tablets, pills, powders, cachets and suppositories. Liquid oral dosage forms include solutions and suspensions. Parenteral preparations include sterile solutions and suspensions. Topical dosage forms can be creams, ointments, lotions, transdermal devices and the like. Except insofar as any conventional media or agent is incompatible with an extract of the invention, use thereof in the pharmaceutical compositions of the invention is contemplated. Supplementary active compounds can also be incorporated into the compositions.

The formulations and pharmaceutical compositions contemplated by the above dosage forms can be prepared with conventional pharmaceutically acceptable excipients and additives using conventional techniques. Such pharmaceutically acceptable excipients and additives are intended to include carriers, binders, flavorings, buffers, thickeners, color agents, stabilizing agents, emulsifying agents, dispersing agents, suspending agents, perfumes, preservatives, lubricants, etc.

Further, the composition can be prepared such that an extract of the invention can be administered in a controlled or time release formulation, for example in a composition which includes a slow release polymer for prolonged release.

Suitable pharmaceutically acceptable solid carriers are magnesium carbonate, magnesium stearate, talc, sugar, lactose, pectin, dextrin, starch, gelatin, tragacanth, methylcellulose, sodium carboxymethylcellulose, low melting waxes, cocoa butter and the like. Capsules can be made wherein the active compound is inserted into pharmaceutically acceptable capsules as a carrier. The active compounds of this invention can be mixed with pharmaceutically acceptable excipients or can be used in finely divided powder form without excipients for inclusion into capsules. Similarly, cachets are included as are liposomes as known to those skilled in the arts.

Liquid form preparations include solutions, suspensions and emulsions. Examples include water or water-propylene glycol solutions for parenteral injection. Liquid preparations can also be formulated in solution in polyethylene glycol and/or propylene glycol, which may contain water. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the active component in the oil form within an emulsifier such as TWEEN™-80 as is known in the industry familiar with oil/water emulsions.

In various embodiments, an extract of the invention may be used cosmetically in formulations for such applications, e.g., to reduce or prevent effects associated with oxidative stress, e.g., of skin. The invention provides corresponding cosmetic methods, in which an extract of the invention is applied or administered in a cosmetically acceptable formulation, e.g., in a suitable topical formulation to a site of interest (e.g., an area of skin). Accordingly, the invention also provides cosmetic compositions comprising an extract of the invention and a cosmetically acceptable excipient, carrier or vehicle.

A cosmetically acceptable excipient, carrier or vehicle that may act as a diluent, dispersant or carrier for the extract of the invention and the other materials that may be present in the composition, so as to facilitate their distribution when the composition is applied to the skin. "Cosmetically acceptable carrier", "cosmetically acceptable excipient" or "cosmetically acceptable vehicle" as used herein refers to one or more compatible solid or liquid fillers, diluents, extenders and the like, which are cosmetically acceptable as defined herein. The term "compatible," as used herein, means that the components of the compositions of this invention are capable of being commingled with the primary active of the present invention (e.g., the extract described herein), and with each other, in a manner such that there is no interaction that would substantially reduce the efficacy of the composition under ordinary use situations. The type of vehicle utilized in the present invention depends on the type of product desired. The vehicles may also include but are not limited to one or more of organic solvents, thickeners, humectants, oils, silicone oils, water, emulsifiers, liquid or solid emollients, propellants and powders. Such mixtures may take several forms, including but not limited to solutions, dispersions, emulsions (O/W, W/O or W/O/W) such as light creams, lotions, serums, and gels. Powders, such as chalk, talc, fullers earth, kaolin, starch, gums, colloidal silica sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose and ethylene glycol monostearate can be selected.

As used herein, "lotions" are liquid cosmetics, often suspensions or dispersions intended for external application to the body.

As used herein, "creams" are soft cosmetic-type preparations. Creams of the oil-in-water (O/W) type include preparations such as foundation creams, hand creams, shaving creams, and the like. Creams of the water-in-oil (W/O) type include cold creams, emollient creams, and the like. Pharmaceutically, creams are solid emulsions containing suspensions or solutions of active ingredients for external application. Generally, preparations of this type are classified as ointments. Specifically, they belong to the emulsion-type bases.

As used herein, "ointments" are semisolid preparations for external application of such consistency that may be readily applied to the skin. They should be of such composition that they soften, but not necessarily melt, when applied to the body. They serve as vehicles for the topical application of active ingredients and also function as protectives and emollients for the skin. For many years ointments were limited by definition and use to mixtures of fatty substances. Today, in addition to such oleaginous mixtures, there are ointment preparations possessing the same general consistency but entirely free of oleaginous substances. In many instances, they are emulsions of fatty or wax-like materials with comparatively high proportions of water. These emulsions may be either water-in-oil (W/O) or oil-in-water (O/W) emulsions, depending primarily on the selection of the emulsifying agent. Such semisolid emulsions are also referred to as creams. Creams and ointments containing large amounts of insoluble powders are referred to as pastes. Pastes are usually stiffer and more absorptive than creams and ointments.

For cosmetic applications, a composition of the invention comprising an extract of the invention may further comprise standard cosmetic ingredients, for example those known in the art to be used as moisturizers, stabilizers, preservatives, scents and the like. The type of cosmetic composition may be, for example, skin care cosmetics such as skin lotion, emulsion, cream, and cleansing agents; make-up cosmetics such as lipsticks and foundation. The cosmetics may be in any form without limitation.

The cosmetic compositions of the present invention may further comprise one or more cosmetic agents or dermatological active agents e.g., agents capable of treating or preventing any sign of aging of the skin. The active agents may be chosen, for example, from skin whitening agents, optical brightening agents, sunscreen agents, moisturizers, free-radical scavengers, keratolytic agents, vitamins, anti-elastase and anti-collagenase agents, peptides, fatty acid derivatives, steroids, trace elements, extracts of algae and of planktons, enzymes and coenzymes, flavonoids and ceramides, alpha-hydroxy acids and mixtures thereof, and enhancing agents.

Other cosmetically or dermatologically acceptable agents that may be used in the compositions of the invention include but are not limited to coloring agents (e.g., pigments, dyes, colorants), preservatives, perfumes and fragrances, pulverulent agents, antiperspirants and/or odor absorbers, natural extracts, procyannidol oligomers, urea, caffeine, fillers, keratolytic agents, extracts of algae, fungi, plants, yeasts or bacteria, hydrolysed, partially hydrolysed or unhydrolysed proteins such as enzymes, antibacterial or bactericidal agents e.g., 2,4,4'-trichloro-2'-hydroxydiphenyl ether (triclosan) and 3,4,4'-trichlorocarbanilide (or triclocarban) and azelaic acid, matt-effect agents, for instance fibres, tensioning agents, and mixtures thereof. Amounts of such agents typically range from about 0.0001% to about 20% by weight of the composition.

The composition may be packaged in a suitable container. The choice of container may depend upon the viscosity and intended use of the composition by the consumer. For example, a lotion or fluid cream can be packaged in a bottle or a roll-ball applicator, or a capsule, or a propellant-driven aerosol device or a container fitted with a pump suitable for finger operation. When the composition is a cream, it can simply be stored in a non-deformable bottle or squeeze container, such as a tube or a lidded jar.

In another aspect, the extract and/or compositions comprising the extract of the present invention can be formulated for administration as foods or dietary supplements using one or more consumable carriers. A "consumable carrier" is herein defined as any food, food ingredient, or food additive, or any excipient utilized for tabletting, encapsulation, or other formulation of an active agent for oral administration, whether for human or animal use. For dietary supplements, the extract can be mixed according to methods routine in the art. Dietary supplements can be prepared in a variety of forms including, but not limited to, liquid, powder, or solid pill forms. The extract or composition of the present invention can be administered either alone or in combination with other compounds or extracts where combining compounds or extracts would lead to additive or synergistic effects. The extract and/or composition of the present invention can also be added directly to foods and ingested as part of a normal meal. Various methods are known to those skilled in the art for addition or incorporation of such agents into foods.

The compositions of the invention herein can comprise, consist essentially of, or consist of, the ingredients and components (e.g., the extract) described herein. "Consisting essentially of" as used herein means that the composition may include additional ingredients, but only if the additional ingredients do not materially alter the basic and novel characteristics of the claimed compositions or methods.

In another aspect, the present invention provides a use of (i) the above-mentioned extract, (ii) the above-mentioned composition, or (iii) a combination of (i) and (ii), as a medicament.

In another aspect, the present invention provides a use of (i) the above-mentioned extract, (ii) the above-mentioned composition, or (iii) a combination of (i) and (ii), for the preparation of a medicament.

In another aspect, the present invention provides a use of (i) the above-mentioned extract, (ii) the above-mentioned composition, or (iii) a combination of (i) and (ii), as an antioxidant.

In another aspect, the present invention provides a use of (i) the above-mentioned extract, (ii) the above-mentioned composition, or (iii) a combination of (i) and (ii), for decreasing or inhibiting oxidative stress in a cell or tissue.

In another aspect, the present invention provides a use of (i) the above-mentioned extract, (ii) the above-mentioned composition, or (iii) a combination of (i) and (ii), for prevention or treatment of a condition associated with oxidative stress.

In another aspect, the present invention provides a use of (i) the above-mentioned extract, (ii) the above-mentioned composition, or (iii) a combination of (i) and (ii), for the preparation of a medicament for decreasing or inhibiting oxidative stress in a cell or tissue.

In another aspect, the present invention provides a use of (i) the above-mentioned extract, (ii) the above-mentioned composition, or (iii) a combination of (i) and (ii), for the preparation of a medicament for prevention or treatment of a condition associated with oxidative stress.

In another aspect, the present invention provides (i) the above-mentioned extract, (ii) the above-mentioned composition, or (iii) a combination of (i) and (ii), for use as a medicament.

In another aspect, the present invention provides (i) the above-mentioned extract, (ii) the above-mentioned composition, or (iii) a combination of (i) and (ii), for use in the preparation of a medicament.

In another aspect, the present invention provides (i) the above-mentioned extract, (ii) the above-mentioned composition, or (iii) a combination of (i) and (ii), for use as an antioxidant.

In another aspect, the present invention provides (i) the above-mentioned extract, (ii) the above-mentioned composition, or (iii) a combination of (i) and (ii), for use in decreasing or inhibiting oxidative stress in a cell or tissue.

In another aspect, the present invention provides (i) the above-mentioned extract, (ii) the above-mentioned composition, or (iii) a combination of (i) and (ii), for use in preventing or treating a condition associated with oxidative stress.

In another aspect, the present invention provides a method of decreasing or inhibiting oxidative stress in a cell or tissue comprising contacting said cell or tissue with (i) the above-mentioned extract, (ii) the above-mentioned composition, or (iii) a combination of (i) and (ii).

In another aspect, the present invention provides a method for preventing or treating a condition associated with oxidative stress in a subject, said method comprising administering to said subject (i) the above-mentioned extract, (ii) the above-mentioned composition, or (iii) a combination of (i) and (ii).

In an embodiment the subject is a mammal, in a further embodiment, a human.

"Oxidative stress" as used herein generally refers to oxidative damage in a cell, tissue, or organ, caused by reactive oxygen species (ROS), such as free radicals and peroxides. The level of oxidative stress is typically determined by the balance between the rate at which oxidative damage is induced and the rate at which it is efficiently repaired and removed.

MODE(S) FOR CARRYING OUT THE INVENTION

The present invention is illustrated in further detail by the following non-limiting examples.

Example 1

Method of Extraction

Green sea urchin (*Strongylocentrotus droebachiensis*) tissues (gonads and digestive system) and sea cucumber (*Cucumaria frondosa*) viscera were freeze-dried for 96 h, finely ground with a commercial grinder (Fitzmill™ D6) to >250 µm size and kept frozen (−20° C.) in the dark for about one week. Dry and ground samples were used for high-pressure liquid-solid extraction (HPLE) based on the method of Richter et al. (U.S. Pat. No. 5,843,311). The extraction process was carried out using a Dionex™ ASE-200 extractor (Dionex Corporation, Sunnyvale, Calif., USA). For each extraction, about 200 mg of ground sample was mixed with a dispersing agent (diatomaceous earth) to facilitate the distribution of the biological material along each extraction cell, and increasing the contact surface with the solvent. For 200 mg of dry sample, 4400 mg of dispersing agent was used (sample/dispersing agent ratio of about 1/22). The dispersing agent and sample mix was introduced in a 11 ml stainless steel extraction cell equipped with 0.22 µm cellulose filter previously installed in the bottom part of the cell, just before the extract collector. Four extraction solvents with different polarities have been used for extraction: water, methanol, ethanol, and isopropanol. The extraction parameters that have been used are given in Table I.

TABLE I

Extraction parameters used for HPLE

| Extraction parameters | Values |
| --- | --- |
| Temperature | 40° C. |
| Pre-heating | 1 minute |
| Heating | 5 minutes |
| Static extraction | 10 minutes |
| Pressure | 1500 psi |
| Purge | 60 seconds |
| Flush volume | 60% |
| Cycle | 1 |

Liquid extracts were obtained in glass collectors previously weighed with precision. The glass bottle collector with the extract was left a few minutes to cool down in dark and weighed again. Then, the extract was stored at 4° C. until analysis. The volume of the extract was determined using the volumetric mass of the solvent and the total weight of the extract. An average of about 14 ml of liquid extract was obtained, which means a weight/volume ratio between initial sample and solvent used of about 1/70.

The mass of dry matter obtained by each extract is then determined by evaporation to dryness of an aliquot of the extract using a continuous nitrogen flow at ambient temperature.

Example 2

Evaluation of the Antioxidant Properties of the Extracts

Antioxidant properties of extracts were estimated using the Oxygen Radical Absorption Capacity (ORAC) method. The analytical procedure has been adapted from a published method (Ou et al., 2001. *J. Agric. Food Chem.* 49: 4619-4626), using 96-well microplates and a SpectraMaxGemini™ spectrofluorometer (Molecular Devices Corporation, Sunnyvale, Calif., USA). After appropriate dilution (typically between 1/100 to 1/1000), a 30-µl aliquot of the extract was added to each well in which 150 µl of 1.04 µM fluorescein and 30 µl of 162 mM 2,2'-azobis (2-amidinopropane) hydrochloride (AAPH) were previously added. Trolox™ (6-hydroxy-2,5,7,8-tetramethylchroman-2-carboxylic acid), a water soluble analog of vitamin E, was used as positive control, and phosphate buffer pH 7.4 was used as the analytical blank. The reactive mixture was incubated at 37.5° C. for 90 min. Final results were calculated as a function of the difference between the surface under the curves between blanks and extracts, and the antioxidant properties expressed as ORAC values in equivalent micromolar of Trolox™ by dry weight of the sample (µmol TE/g extract).

Example 3

Effect of Extraction Solvent and Tissue on the Antioxidant Properties of the Extract The ORAC results show that extracts having antioxidant properties from three different echinoderm tissues were obtained using the HPLE extraction process. As shown in Table II, the ORAC values typically vary depending on the tissue from which the extract is obtained and on the nature of solvent used. The ORAC results also show a general trend of an increasing antioxidant power following the solvent in the series: water<methanol<ethanol<isopropanol, with the exception of sea cucumber viscera where the ethanol extract exhibits an antioxidant power greater than the isopropanol extract. Therefore, extracts having antioxidant properties have been obtained from three different tissues and using four different solvents; use of ethanol and isopropanol yields extracts having more potent antioxidant properties.

TABLE II

ORAC values for different tissues and extraction solvents

| Extraction solvent | ORAC values ($\mu$mol TE/g dry extract) | | |
|---|---|---|---|
| | Digestive tract - Sea Urchin | Gonads - Sea Urchin | Viscera - Sea Cucumber |
| Distilled water | 132 | 108 | 54 |
| Methanol | 953 | 1126 | 827 |
| Ethanol | 4265 | 2652 | 4421 |
| Isopropanol | 6702 | 8630 | 3464 |

Example 4

Effect of Extraction Temperature on the Antioxidant Properties of the Extract

Dry and ground tissues were HPLE extracted using the Dionex extractor and the parameters described in Example 1 above, except for the temperature of extraction that was varied (40, 60 or 80° C.). Ethanol and isopropanol were used as extraction solvents. The methods to collect and preserve the extracts as well as to calculate dry extract yield were similar to those described in Example 1. The extracts were then tested for antioxidant properties using the ORAC assay.

For both extraction solvents, extraction temperatures of 60° C. and 80° C. yielded extracts having ORAC values generally higher as compared to extracts obtained at 40° C. (Table III). Also, extraction at 60° C. resulted in extracts having mean ORAC values slightly higher than extracts obtained at 80° C., with the exception of the ethanol extract obtained from urchin digestive tract (Table III). An additional test conducted to evaluate the short-term stability of extracts obtained at 80° C. indicated that they are less stable at room temperature (about 22° C.) and at 4° C. than the extracts obtained at 40° C. and 60° C. The appearance of a white residue at the bottom of the glass bottle collectors of 80° C. extracts suggests that one or more component(s) of the extract precipitated after 24 h. This precipitation was not observed, even after 3 months, in extracts obtained at 40° C. and 60° C.

TABLE III

ORAC values of extracts obtained at different temperatures

| Extraction temperature (° C.) | ORAC values ($\mu$mol TE/g dry extract) | | | | | |
|---|---|---|---|---|---|---|
| | Digestive tract - Sea Urchin | | Gonads - Sea Urchin | | Viscera - Sea Cucumber | |
| | Ethanol | Isopropanol | Ethanol | Isopropanol | Ethanol | Isopropanol |
| 40 | 4265 | 6701 | 2652 | 8629 | 4420 | 3463 |
| 60 | 4930 | 8709 | 4061 | 10148 | 5390 | 4204 |
| 80 | 5203 | 6819 | 3617 | 9200 | 4903 | 4032 |

Example 5

Comparison of the Antioxidant Properties of the Dry Extracts with Known Antioxidants The dry extract was prepared by evaporation of the extraction solvent using two methods, either under a continuous nitrogen flux or using a rotating evaporator. These two methods yielded extracts having similar antioxidant properties. It was observed that evaporation at a temperature of about 25 to 30° C. significantly shortened the time required to evaporate the solvent without affecting the antioxidant properties of the extract. In an attempt to minimize potential degradation of antioxidant properties, it is preferable that all operations be conducted under low light intensity. In order to test the stability of ORAC capacity (i.e., antioxidant properties) for each dry extract, an aliquot of about 150-200 mg of dry extract was stored in an amber vial, carefully capped and kept in the refrigerator (at about 4° C.) for 3 months. ORAC analysis was then performed on these stored extracts.

The dry extracts were opaque viscous concentrates of orange color for sea urchin digestive system ($\lambda$max=460-465 nm), yellow for sea urchin gonads ($\lambda$max=450-455 nm) and reddish for sea cucumber viscera ($\lambda$max=475-480 nm). After a 3-month storage in previously described conditions, physical appearance and antioxidant properties remained unchanged.

The antioxidant properties of extracts obtained at 60° C. using two different extraction solvents (ethanol or isopropanol) were compared to known pure antioxidants such as $\alpha$-tocopherol, catechin and $\beta$-carotene. Values were also compared to ORAC scores of antioxidant extracts available in the literature. The ORAC values of the extracts were generally higher than that of $\beta$-carotene (Table IV). The isopropanol extracts of sea urchin digestive tract and gonads showed antioxidant potency significantly higher than that of $\alpha$-tocopherol. The ORAC values for other extracts are similar to, or lower than, the ORAC values of $\alpha$-tocopherol. All extracts generally have ORAC values below that of catechin. However, ORAC values of the extracts are higher than most essential oils of therapeutic grade, generally considered the most powerful natural antioxidant extracts.

TABLE IV

ORAC values of the extracts prepared herein and of known antioxidants

| Extract | ORAC values (µmol TE/g dry extract) |
|---|---|
| Digestive tract - Sea Urchins | |
| Ethanol | 4930 |
| Isopropanol | 8709 |
| Gonads - Sea Urchins | |
| Ethanol | 4061 |
| Isopropanol | 10148 |
| Viscera - Sea Cucumber | |
| Ethanol | 5390 |
| Isopropanol | 420 |
| Pure antioxydants* | |
| β-carotene | 3183 |
| α-Tocopherol | 5657 |
| Catechin | 16601 |
| Essential oils** | |
| Clove tree | 10787 |
| Thyme | 160 |
| Oregano | 153 |
| Ceylan cinnamon | 103 |
| Savory mountain | 113 |

*Values obtained by analyses performed in the present studies.
**Values published in: "The Essential Oils Desk Reference, 4th Edition, Essence Science Publishing, 558 pages"

Example 6

Composition of the Extract

The amount of various antioxidant compounds in the extracts was assessed. For the analysis of α-tocopherol content, dry extracts were re-dissolved in extraction solvent and filtered on a 0.45 µm filter to remove insoluble material. A volume of 2 ml of re-dissolved extract was evaporated to dryness under nitrogen flux and the remaining solid was re-dissolved in 2 ml of a hexane/methanol mixture (50/50). 100 µl of distilled water was added to the solution to allow a separation of two phases: a hexane phase and a methanol+water phase. The hexane phase was separated and an aliquot of 1 ml was taken and evaporated to dryness and then submitted to derivatization by silylation using N-tert-butyldimethylsilyl-N-methyltrifluoroacetamide (MTBSTFA). The derivatized extract was injected in splitless mode in a gas chromatograph, model Varian™ CP 3800, coupled to a mass spectrometer, model Varian™ Saturn 2200 (Varian Inc., Palo Alto, Calif., USA) for the separation, identification and quantification of searched compounds. Separation of compounds was obtained with a capillary non-polar column, Simplicity-1, 0.25 mm ID×30 m, 0.25 µm coating thickness.

Carotenoids and total phenols were analysed by a spectrophotometric method. For each extract, after appropriate dilution with the extraction solvent, a 1 ml aliquot was added to a 1 ml graduated test tube with 4 ml of diethyl ether and 4 ml of distilled water. The mixture was vigorously stirred and then centrifuged at 3500 rpm for 2 min to separate the organic phase containing the carotenoids and the aqueous phase containing the phenols. Both phases were evaporated to dryness under nitrogen flux. The aqueous phase was warmed to 30° C. to reduce evaporation time. The resulting dry residues from the organic phase were re-suspended in acetone and those from the aqueous phase in distilled water in an appropriate dilution to reach concentration ranges used with calibration curves. Total carotenoids were analysed by spectrophotometry at 447 nm and the quantification was conducted using standard solutions of β-carotene ranging from 2 to 200 mg/g (Arena et al., 2000. *J. Food Sci.* 65: 458-460; Symonds et al., 2007. *Comp. Biochem. Physiol. B* 148: 432-444). Total phenols were analysed by the method of Singleton et al. (Singleton et al., 1999. *Methods in Enzymology* 299: 152-178) using Folin-Ciocalteau's reagent and the quantification using standard solutions of gallic acid ranging between 200 and 2000 µg/g. For total phenols, results are presented as the amount (in µg) of gallic acid equivalents per gram (g) of dry extract. The identification of carotenoid chemical species was conducted by liquid phase chromatography coupled to a mass spectrometer (LC-MS), model Thermo Finnigan™ LCQ Advantage (Thermo Fisher Scientific Inc. Waltham, Mass., USA). The separation was obtained with a reverse phase column Agilent-Zorbax™ SB-C18 4.6 mm ID×250 mm, 5 µm and the identification of carotenoids was performed by comparing retention times of unknown compounds with those of known molecules such as fucoxanthin, astaxanthin and β-carotene, and also by examining their mass spectra with library spectra.

Concentrations of α-tocopherol, carotenoids and total phenols as a function of extraction solvents and tissue extracted are presented in Table V. In general, the extracts obtained using ethanol showed the highest levels in these three potential antioxidants as compared to isopropanol extracts, with certain particular cases. Isopropanol extracts of sea urchin digestive system and gonads are enriched in α-tocopherol and total phenols, respectively, as compared to corresponding extracts obtained using ethanol. With respect to the carotenoids composition, sea urchin extracts contain more fucoxanthinol whereas sea cucumber viscera contained higher levels of cucumariaxanthin and canthaxanthin, two natural derivatives of astaxanthin.

TABLE V

Concentration of α-tocopherol, total carotenoids and total phenols in different extracts obtained at an extraction temperature of 60° C.

| Compounds | Digestive tract - Sea Urchin | | Gonads - Sea Urchin | | Viscera - Sea Cucumber | |
|---|---|---|---|---|---|---|
| | Ethanol | Isopropanol | Ethanol | Isopropanol | Ethanol | isopropanol |
| α-Tocopherol (µg/g) | 310 | 703 | 377 | 229 | 220 | 145 |
| Total carotenoids (mg/g) | 80 | 114 | 75 | 10 | 60 | 33 |
| Total phenols (µg/g) | 1051 | 965 | 794 | 1246 | 894 | 464 |

A correlation study of ORAC values of extracts as a function of their content in the above-mentioned antioxidant compounds was performed. The correlation coefficients ranged from 0.52 to 0.73 (FIG. 1, panels A-C). However, the relatively low α-tocopherol and total carotenoid content of the isopropanol extract of sea urchin gonads coupled to its high ORAC value (10148 μmol TE/g) indicate that one or more other compound(s) having antioxidant properties is/are present in this extract.

Example 7

Fatty Acid Analysis of Extracts

Fatty acid analysis of extracts prepared from sea cucumber viscera, sea urchin gonad and sea urchin gut was assessed as described below.

Chemicals:

Fatty acid methyl ester standards, Supelco™ 37 FAME Mix and $BF_3$-methanol were purchased from Sigma-Aldrich. Helium and nitrogen gas were HP+ grade. All solvents were HPLC grade.

Derivatization:

An aliquot of 1 ml extract was evaporated to dryness under nitrogen flux. Dried extract was dissolved in 0.5 ml hexane, and 1 ml of $BF_3$-methanol was added. The mixture was shaken and put in a 60° C. hot bath for 30 minutes. The mixture was cooled down to room temperature for 10 min. 0.5 ml of deionized water and 2 ml of hexane were added to the mixture. The resulting solution was shaken, centrifuged and the organic phase was recovered. This operation was repeated twice. The organic phase was then purified by passing through a column of sodium sulfate (1 cm height, 5 mm internal diameter) to eliminate water residue. About 4.5 ml of the final solution was collected and frozen at −20° C. until GC-MS analysis.

GC-MS Analysis:

Fatty acid methyl esters (FAME) were separated using Trace™ GC (ThermoFinnigan, USA), equipped with VB-5® capillary column (30 m×0.25 mm i.d; Valcobond, USA), coupled with PolarisQ™ mass spectrometer (ThermoFinnigan, USA). Helium was the carrier gas used. Ion detection was made using positive mode with mass interval of 60-650 amu. A calibration curve was made with concentration a range of FAME mix, from 6.25 μg ml$^{-1}$ to 100 μg ml$^{-1}$. Data acquisition and chromatogram treatment were carried out using Xcalibur® 1.3 software (ThermoFinnigan, USA). A final concentration was calculated for each FAME using the external calibration curve mentioned above.

Results are presented in Table VI below.

TABLE VI

Concentration of various fatty acids in extracts obtained at an extraction temperature of 60° C.

| | Fatty acid composition of echinoderm extracts (as % of total fatty acids) | | | | | |
|---|---|---|---|---|---|---|
| | 60° C.-Ethanol extracts | | | 60° C.-Isopropanol extracts | | |
| Fatty acids | SCV | UGON | UGUT | SCV | UGON | UGUT |
| Saturated | 24 | 32 | 27 | 24 | 31 | 33 |
| Monoinsaturated | 33 | 30 | 24 | 31 | 28 | 30 |
| Polyinsaturated | 44 | 38 | 49 | 45 | 41 | 37 |
| ω-3: ALA | 0.4 | 0.3 | 0.4 | 0.4 | 0.4 | 0.3 |
| EPA | 28.5 | 10.4 | 12.2 | 29.9 | 14.9 | 10.4 |
| DHA | 0.2 | 0.2 | 2.9 | 3.5 | 0.0 | 0.0 |

TABLE VI-continued

Concentration of various fatty acids in extracts obtained at an extraction temperature of 60° C.

| | Fatty acid composition of echinoderm extracts (as % of total fatty acids) | | | | | |
|---|---|---|---|---|---|---|
| | 60° C.-Ethanol extracts | | | 60° C.-Isopropanol extracts | | |
| Fatty acids | SCV | UGON | UGUT | SCV | UGON | UGUT |
| Total ω-3 | 33.6 | 25.0 | 30.8 | 37.9 | 23.1 | 25.3 |
| Total ω-6 | 6.3 | 10.2 | 10.7 | 6.3 | 14.7 | 9.3 |
| ω-6/ω-3 | 0.2 | 0.4 | 0.3 | 0.2 | 0.6 | 0.4 |
| ω-3/ω-6 | 5.3 | 2.4 | 2.9 | 6.1 | 1.6 | 2.7 |

SCV: Sea cucumber viscera
UGON: Sea urchin gonad
UGUT: Sea urchin gut
ALA: alpha-linolenic acid
EPA: eicosapentaenoic acid
DHA: docosahexaenoic acid Although the present invention has been described hereinabove by way of specific embodiments thereof, it can be modified, without departing from the spirit and nature of the subject invention as defined in the appended claims. The articles "a," "an" and "the" are used herein to refer to one or to more than one (i.e., to at least one) of the grammatical object of the article. The terms "including" and "comprising" are used herein to mean, and are used interchangeably with, the phrases "including but not limited to" and "comprising but not limited to".

What is claimed is:

1. An Echinozoa tissue or organ extract having an Oxygen Radical Absorption Capacity (ORAC) value of at least 4000 micromolar of Trolox® (6-hydroxy-2,5,7,8-tetramethylchroman-2-carboxylic acid) equivalent (TE) per gram of the dry extract.

2. An Echinozoa tissue or organ extract obtained by high-pressure liquid-solid extraction (HPLE) at a temperature of 40° C. to 80° C. using an alcohol as the extracting solvent, wherein the high pressure is at least 100 psi.

3. The extract of claim 2, wherein said extract has (a) an ORAC value of at least 4000 micromolar of Trolox® (6-hydroxy-2,5,7,8-tetramethylchroman-2-carboxylic acid) equivalent (TE) per gram of the dry extract.

4. The extract of claim 3, wherein said extract has (a) an ORAC value of at least 5000 micromolar of TE per gram of the dry extract.

5. The extract of claim 1, wherein said tissue or organ comprises (i) a gonad, (ii) a tissue or organ of the digestive tract, (iii) a viscus, or (iv) any combination of (i) to (iii).

6. The extract of claim 1, wherein said Echinozoa is of the Holothuroidea or Echinoidea class.

7. The extract of claim 1, wherein said extract comprises (i) at least 100 μg of α-Tocopherol per gram of extract, (ii) at least 10 mg of carotenoids per gram of extract, (iii) at least 400 μg of phenols per gram of extract, or (iv) any combination of (i) to (iii).

8. A process for preparing an Echinozoa tissue or organ extract having an Oxygen Radical Absorption Capacity (ORAC) value of at least 4000 micromolar of Trolox® (6-hydroxy-2,5,7,8-tetramethylchroman-2-carboxylic acid) equivalent (TE) per gram of the dry extract, comprising the steps of:
(a) providing ground Echinozoa tissue or organ;
(b) mixing said ground tissue or organ with a dispersing agent; and (c) submitting said mixture to high-pressure liquid-solid extraction (HPLE) at a temperature of 40° C. to 80° C. using an alcohol as the extracting solvent, wherein the high pressure is at least 100 psi.

9. The process of claim 8, further comprising (d) evaporating the solvent from the extract of step (c).

10. The process of claim 8, further comprising freeze-drying or dehydrating said Echinozoa tissue or organ before step (a).

11. The process of claim 8, wherein said dispersing agent is diatomaceous earth.

12. The process of claim 8, wherein the tissue or organ/dispersing agent ratio is from about 1/10 to about 1/30 (w/w).

13. The process of claim 8, wherein the tissue or organ/dispersing agent ratio is about 1/22 (w/w).

14. The process of claim 8, wherein said extraction is performed at a temperature of 40° C. to 60° C.

15. The process of claim 8, wherein said alcohol is an alcohol of formula I:

(I)

wherein $R^1$ and $R^2$ are each independently $CH_3$ or H;
or any combination of (i) an alcohol of formula I wherein $R^1$ and $R^2$ are H, (ii) an alcohol of formula I wherein $R^1$ is $CH_3$ and $R^2$ is H, and (iii) an alcohol of formula I wherein $R^1$ and $R^2$ are $CH_3$.

16. The process of claim 8, wherein said extract has (a) an eicosapentaenoic acid (EPA) to docosahexaenoic acid (DHA) ratio of at least 4; (b) an eicosapentaenoic acid (EPA) content of at least 10% of the total fatty acid content; (c) an omega-3 ($\omega$-3) to omega-6 ($\omega$-6) fatty acid ratio of at least 1.6 (w/w); or (d) any combination of (a) to (c).

17. The process of claim 16, wherein said extract has an ORAC value of at least 5000 micromolar of TE per gram of the dry extract.

18. The process of claim 8, wherein said extract comprises (i) at least 100 µg of $\alpha$-Tocopherol per gram of extract, (ii) at least 10 mg of carotenoids per gram of extract, (iii) at least 400 µg of phenols per gram of extract, or (iv) any combination of (i) to (iii).

19. The extract of claim 1, wherein said extract has; (a) an eicosapentaenoic acid (EPA) to docosahexaenoic acid (DHA) ratio of at least 4; (b) an eicosapentaenoic acid (EPA) content of at least 10% of the total fatty acid content; (c) an omega-3 ($\omega$-3) to omega-6 ($\omega$-6) fatty acid ratio of at least 1.6 (w/w); or (d) any combination of (a) to (c).

20. The extract of claim 3, wherein said extract has; (a) an eicosapentaenoic acid (EPA) to docosahexaenoic acid (DHA) ratio of at least 4; (b) an eicosapentaenoic acid (EPA) content of at least 10% of the total fatty acid content; (c) an omega-3 ($\omega$-3) to omega-6 ($\omega$-6) fatty acid ratio of at least 1.6 (w/w); or (d) any combination of (a) to (c).

21. The process of claim 15, wherein $R^1$ and $R^2$ are $CH_3$.

* * * * *